United States Patent [19]

Hsieh

[11] Patent Number: 4,480,034

[45] Date of Patent: Oct. 30, 1984

[54] CONTINUOUS FERMENTATION PROCESS AND BIOCONVERSION-PRODUCT RECOVERY

[75] Inventor: Jih-Han Hsieh, Parsippany, N.J.

[73] Assignee: Celanese Corporation, New York, N.Y.

[21] Appl. No.: 387,084

[22] Filed: Jun. 10, 1982

[51] Int. Cl.$^3$ .......................... C12P 7/44; C12N 1/28; C12M 1/36; C12M 1/12

[52] U.S. Cl. .................................... 435/136; 435/142; 435/189; 435/190; 435/245; 435/248; 435/249; 435/253; 435/289; 435/291; 435/311; 435/813; 435/877

[58] Field of Search ............... 435/136, 142, 189, 190, 435/253, 245, 248, 249, 813, 877, 291, 289, 311

[56] References Cited

U.S. PATENT DOCUMENTS

| | | | |
|---|---|---|---|
| 2,686,754 | 8/1954 | Monod | 435/813 |
| 2,822,319 | 2/1958 | Monod | 435/813 |
| 3,729,378 | 4/1973 | Imai et al. | 435/136 |
| 4,124,449 | 11/1978 | Barta et al. | 435/311 |
| 4,167,450 | 9/1979 | Chesbro et al. | 435/813 |
| 4,209,585 | 6/1980 | Lloyd et al. | 435/311 |
| 4,276,384 | 6/1981 | Mueller et al. | 435/311 |
| 4,355,107 | 10/1982 | Maxwell | 435/253 |
| 4,382,965 | 5/1983 | Sandine et al. | 435/253 |

OTHER PUBLICATIONS

*Dictionary of Organic Compounds,* vol. 2, Oxford University Press, New York, N.Y. (1936) p. 841.

*Primary Examiner*—Thomas G. Wiseman
*Assistant Examiner*—Deborah A. Grossman
*Attorney, Agent, or Firm*—Depaoli & O'Brien

[57] ABSTRACT

This invention provides a continuous bioconversion process in which a cross-flow membrane filtration zone is employed to recover a whole cell-containing retentate stream and a cell-free bioconversion product-containing permeate stream. The retentate stream is recycled to the fermentation zone. In a specific embodiment, toluene is bio-oxidized to muconic acid with a microorganism such as *Pseudomonas putida* Biotype A strain ATCC 31,916. The muconic acid is recovered as a precipitate from the cell-free permeate fermentation broth, and the fermentation broth is recycled in the process.

13 Claims, 1 Drawing Figure

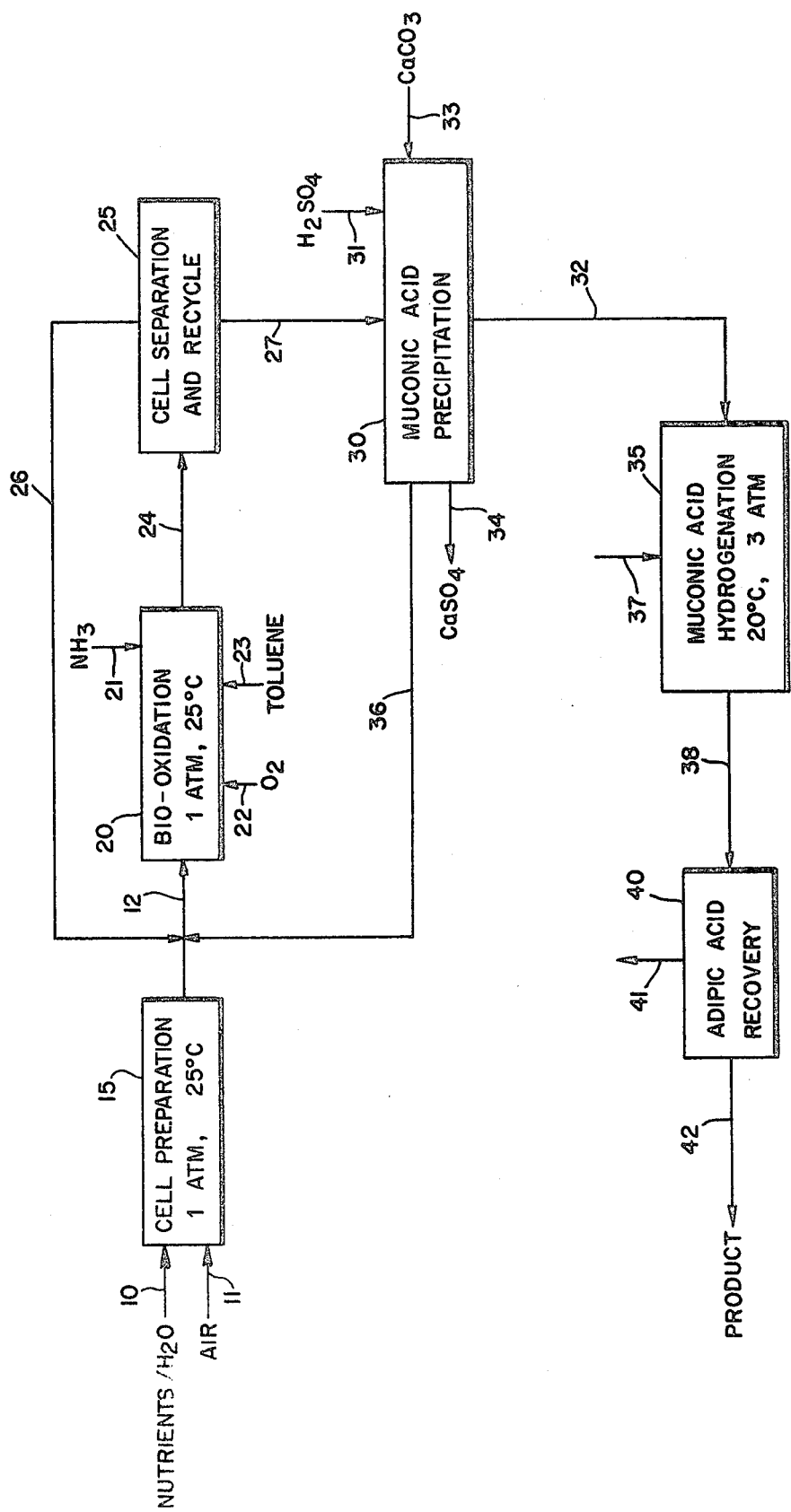

CONTINUOUS FERMENTATION PROCESS AND BIOCONVERSION-PRODUCT RECOVERY

BACKGROUND OF THE INVENTION

Carboxylic acids are important high volume commodities in the chemical industry. For example, it is estimated that the 1982 worldwide capacity for adipic acid is about five billion pounds.

Adipic acid is produced by oxidation of cyclohexane or cyclohexanol with nitric acid in the presence of a vanadium-copper catalyst. Other methods of synthesizing adipic acid include 1,3-butadiene carbonylation with carbon monoxide followed by hydrolysis; methyl acrylate dimerization; and 1,4-butanediol carbonylation.

The surge of recent biotechnical advances has increased interest in the potential application of bioconversion systems for the production of high volume chemicals such as adipic acid and other carboxylic acids and commercially established commodities.

One prospective new method of synthesizing a carboxylic acid such as adipic acid is by the hydrogenation of muconic acid, which is a diolefinically unsaturated adipic acid derivative:

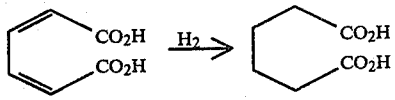

A potentially convenient source of muconic acid is by the microbiological oxidation of various hydrocarbon substrates. Microbiological oxidation of hydrocarbons is reviewed in Applied Microbiology, 9(5), 383(1961) and in "Advances in Enzymology", 27 469-546(1965) by Interscience Publishers.

The Journal of Biological Chemistry, 241(16), 3776 (1966) reports the conversion of catechol and protocatechuate to $\beta$-ketoadipate by *Pseudomonas putida*. The conversion of catechol proceeds by the ortho pathway via a muconic acid intermediate:

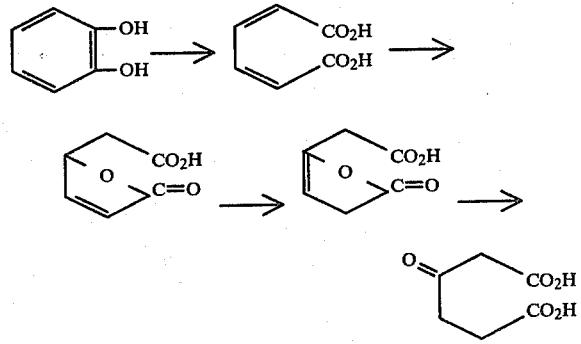

The chemical structures illustrated in the reaction scheme are catechol, muconic acid, muconolactone, $\beta$-ketoadipate enollactone and $\beta$-ketoadipate, respectively.

In the Journal of Bacteriology, 135, 756(1978) there is reported a study of the ubiquity of plasmids in coding for toluene and xylene metabolism in soil bacteria. One of the mutant strains of *Pseudomonas putida* isolated had the ability to metabolize toluene via benzyl alcohol, benzaldehyde, benzoic acid and catechol by the ortho pathway through $\beta$-ketoadipate to a biomass and carbon dioxide.

The enzymes functioning in the toluene metabolism by the ortho pathway included toluene mono-oxygenase, benzyl alcohol dehydrogenase, benzaldehyde dehydrogenase, benzoate oxygenase, dihydrodihydroxybenzoate dehydrogenase, catechol 1,2-oxygenase and muconate lactonizing enzyme. The subsequently formed $\beta$-ketoadipate was further assimilated to biomass and carbon dioxide. The mutant strains that metabolized toluene via the ortho pathway did not accumulate muconic acid, since the said muconic acid metabolite was further transformed in the presence of muconate lactonizing enzyme.

No known naturally occurring microorganisms (e.g., *Pseudomonas putida*) are known that metabolize an aromatic hydrocarbon substrate such as toluene by the ortho pathway via muconic acid and $\beta$-ketoadipate. Wild strains metabolize aromatic hydrocarbon substrates by the meta pathway via 2-hydroxymuconic semialdehyde instead of a muconic acid intermediate. Catechol 2,3-oxygenase is functional rather than catechol 1,2-oxygenase.

Thus, the potential of microbiological oxidation of toluene as a convenient source of muconic acid requires the construction of mutant strains of microorganisms which (1) metabolize toluene by means of the ortho pathway, and (2) allow the accumulation of muconic acid without further assimilation.

The said construction of the desirable mutant strains recently has been achieved, as exemplified by *Pseudomonas putida* Biotype A strain ATCC No. 31,916.

As a consequence of the prospect of large scale bioconversion systems for production of carboxylic acid type compounds from lower cost hydrocarbon substrates, the problems of fermentation system stability, effective biocatalyst activity and consequential bioconversion product formation and accumulation, and of efficient recovery of bioconversion products contained as low concentration solutes in fermentation culture media are of increasing significance. Further, an ancillary concern relates to the storage or disposal of prospective waste streams which are generated by the bioconversion systems.

Accordingly, it is an object of this invention to provide improved methods for the production and recovery of metabolic products in bioconversion systems.

It is another object of this invention to provide a process for the production and separation and recovery of carboxylic acids which are contained as bioconversion products in aqueous fermentation culture media.

It is a further object of this invention to provide a continuous process for the production of extracellular muconic acid product in an aqueous fermentation medium in which a toluene substrate is bio-oxidized, and which process yields a recoverable cell-free fermentation broth which is recycled in the bioconversion system.

Other objects and advantages will become apparent from the accompanying description and examples.

DESCRIPTION OF THE INVENTION

One or more objects of the present invention are accomplished by the provision of an improvement in a microbial bioconversion process in which a non-growth organic substrate in an aqueous fermentation zone is bio-oxidized by intracellular enzyme activity of whole cells to an extracellular water-soluble product having a molecular weight of less than about 5000, the improvement which comprises continuously feeding an aqueous nutrient stream into the fermentation zone, continuously withdrawing whole cell-containing fermentation broth from the fermentation zone, continuously passing the withdrawn fermentation broth through a cross-flow membrane filtration zone, recovering a whole cell-containing retentate stream and a cell-free product-containing permeate stream from the filtration zone, and recycling the retentate stream to the fermentation zone.

In one of its embodiments, the present invention provides an improved microbial bioconversion process in which a non-growth aromatic hydrocarbon substrate in an aqueous fermentation zone is bio-oxidized by intracellular enzyme activity of whole cells to an extracellular water-soluble carboxylic acid product having a molecular weight less than about 1000, which process comprises (1) continuously feeding an aqueous nutrient-limited stream into the fermentation zone; (2) continuously withdrawing whole cell-containing fermentation broth from the fermentation zone; (3) continuously passing the withdrawn fermentation broth through a cross-flow membrane filtration zone; (4) recovering a whole cell-containing retentate stream from the filtration zone, and recycling the retentate stream to the fermentation zone; and (5) recovering a cell-free product-containing permeate stream from the filtration zone, separating the product from the permeate stream, and recycling the resultant permeate stream to the fermentation zone.

The invention process generally is applicable for the production and recovery of carboxylic acid metabolites which accumulate as extracellular products, and particularly carboxylic acids which in the free acid form has a solubility of less than about 1.0 weight percent in an aqueous fermentation medium under ambient conditions, e.g., at about 20°–30° C., and at a fermentation medium pH of less than about 3.0.

Illustrative of carboxylic acid metabolites which can be produced and separated and recovered from fermentation media include aliphatic and aromatic carboxylic acids such as pyruvic acid, butanoic acid, hexanoic acid, succinic acid, glutaric acid, ketoadipic acid, muconic acid, α,α-dimethylmuconic acid, β-carboxymuconic acid, benzoic acid, alkylbenzoic acid, salicylic acid, phenylacetic acid, phenylpyruvic acid, nicotinic acid, and the like.

The cross-flow membrane filtration system employed can be selected from the various hollow fiber, tube, plate and frame, and spiral wound types of modular ultrafiltration systems which have been developed and are available as commercial products.

Romicon (Woburn, Mass.) markets polysulfone membrane hollow fiber or tube ultrafiltration systems. Millipore (Bedford, Mass.) has available plate and frame cassette and spiral wound modular ultrafiltration systems, with cellulosic polymer, polysulfone and polyimide types of membranes. Dorr-Oliver (Westport, Conn.) sells a plate and frame ultrafiltration system with a polysulfone type of membrane. Other commercially available cross-flow filtration systems are produced by companies such as Osmonics (Minnetonka, Minn.), DDS (Nakskov, Denmark), Abcor (Wilmington, Mass.), Nuclearpore (Calif.) and N-D-A (New York).

The term "nutrient-limited" as employed herein refers to an essential fermentation parameter with respect to cell stability, as more fully disclosed in copending patent application Ser. No. 483,796, filed Apr. 11, 1983 (incorporated by reference).

In a continuous fermentation (or chemostat) for cultivation of microorganisms, "growth nutrient-limitation" is necessary in order to achieve a "steady state", i.e., a constant level of cell concentration in a continuous flow reactor with a defined medium composition. The nutrient can be growth carbon, nitrogen, phosphate, sulfate, potassium, magnesium or any other growth-requiring trace metals, and/or oxygen in the case of aerobic fermentation.

The theory and practice of "nutrient-limitation" effects in fermentation systems is elaborated in the literature and in a number of standard textbooks such as Fermentation And Enzyme Technology (John Wiley & Sons, New York, 1979).

As indicated in the literature, conventional nutrient-limitation is primarily a technique to achieve steady state continuous fermentation and to study various yield and maintenance factors of cell mass with respect to various nutrients for cell growth. For the production of conventional fermentation products, such as ethanol, citric acid, lactic acid, acetic acid, and the like (primary metabolites), or antibiotics, microbial toxins, and the like (secondary metabolites) in a continuous flow reactor, nutrient-limitation can also be used to achieve steady state product formation. However, this type of nutrient-limitation has little or no effect on the stability of cells, i.e., the maintenance of the production and productivity level of a specific metabolite.

For a *Pseudomonas putida* Biotype A strain ATCC No. 31,916 type of mutant strain, the cells grow on a preferred growth carbon and energy source (glucose, succinate or acetate) and convert a non-growth carbon (e.g., toluene) to a product (e.g., muconic acid). The mutant strain prefers not to grow on toluene as a carbon source. However, in the presence of toluene and other nutrients over a prolonged period of time (1–2 days), the mutant strain has the tendency to "revert"; i.e., exhibit the ability to grow on toluene again. Initially a small population of the cells reverts, and eventually the majority of the cell population reverts. This reversion problem is unique for these genetically manipulated microorganisms in bioconversion systems.

The application of nutrient-limitation to suppress this reversion phenomenon in bioconversion systems is novel. Thus, for microbial bioconversion processes, the nutrient-limitation aspect can be applied not only to achieve steady state production of cells and product, but also to improve the stability of cells.

For actively growing cells, the growth carbon can be limited to reduce catabolite repression and to increase the level of enzyme induction. Under nitrogen or phosphate or other nutrient-limited conditions, the cell growth is restricted, with the result that the cells selectively grow on a preferred carbon source, such as glucose, succinate or acetate, instead of growing on toluene or other non-growth carbon source. Consequently, the stability of a *P. putida* type of mutant strain is improved. This growth state can be found in continuous fermentation (chemostat) and in the early stage of fed-batch fermentations.

For resting or non-growing cells under nutrient-limitation, a present invention mutant strain, after proper induction to induce enzymes and in the absence of a growth nutrient, converts toluene to muconic acid and obtains energy from the reaction for cell maintenance, and concomitantly achieves cell stability. This situation can be found in the stationary growth phase (or later period) of a fed-batch fermentation, and in the concentrated cells of a continuous fermentation, and in the concentrated cells of a continuous fermentation with cell recycle.

It has been found that in order to achieve higher reactor productivity for muconic acid production the excess energy generated by the bioconversion needs to be removed. During a continuous fermentation with cell recycle, a minimal amount of growth carbon and other nutrients is required for maintenance, and for growth as an energy sink to remove the excess energy generated.

Illustrative of a further embodiment, the present invention provides a microbial bioconversion process in which a toluene substrate in an aqueous fermentation zone is bio-oxidized by intracellular enzyme activity of whole cells to an extracellular muconic acid product, which process comprises (1) maintaining approximately neutral pH conditions in the fermentation zone by the addition of ammonia during the bioconversion period; (2) continuously feeding an aqueous nutrient-limited stream into the fermentation zone; (3) continuously withdrawing whole cell-containing fermentation broth from the fermentation zone; (4) continuously passing the withdrawn fermentation broth through a cross-flow membrane filtration zone; (5) continuously recovering a whole cell-containing retentate stream from the filtration zone, and recycling the retentate stream to the fermentation zone; (6) continuously recovering a cell-free ammonium muconate-containing permeate stream from the filtration zone; (7) adding sulfuric acid or phosphoric acid to the permeate stream to precipitate muconic acid; (8) separating the muconic acid product from the permeate stream, and subsequently treating the permeate stream with a basic reagent selected from metal hydroxides, oxides and carbonate compounds which causes the precipitation of a water-insoluble metal salt; and (9) separating the metal salt precipitate to provide a resultant permeate stream containing a water-soluble ammonium compound, and recycling the said permeate stream to the fermentation zone.

The toluene component referred to above is a "non-growth" organic substrate. The microorganism does not metabolize the substrate for cell growth. Typical non-growth substrates for purposes of the present invention include substituted and unsubstituted aromatic compounds such as benzene, xylene, ethylbenzene, phenol, catechol, naphthalene, and the like.

The addition of the sulfuric acid or phosphoric acid to the cell-free fermentation medium as described above converts ammonium muconate to its free carboxylic acid form. Under the acidic conditions (e.g., a pH of less than about 3) the muconic acid product precipitates out of solution. It is readily separated from the aqueous fermentation medium by filtration or other conventional means.

The acidic aqueous fermentation broth which remains after removal of the muconic acid precipitate is then neutralized with a basic reagent selected from metal hydroxides, metal oxides and metal carbonates which interact with water-soluble ammonium sulfate or ammonium phosphate to form a water-insoluble sulfate or phosphate salt.

Illustrative of suitable basic reagents are the hydroxides, oxides and carbonates of metals such as magnesium, calcium, zinc and barium. Calcium carbonate is the preferred basic reagent.

After the removal of the water-insoluble metal salt precipitate from the treated fermentation broth, the resultant fermentation broth is suitable for recycle to the fermentation zone. The recycle fermentation broth contains a water-soluble ammonium compound, such as ammonium hydroxide or ammonium carbonate.

Because of the presence of the ammonium compound in the recycle fermentation broth, the quantity of ammonia added to the bioconversion zone as previously described can be reduced in an amount corresponding to the ammonium compound molar content in the recycle fermentation broth. The recycle fermentation broth is usually sterilized before it is introduced into the fermentation zone.

The invention is illustrated further by reference to the FIGURE, which is a schematic flow diagram of a combination of processing embodiments for the overall conversion of toluene to adipic acid as per the following stoichiometry:

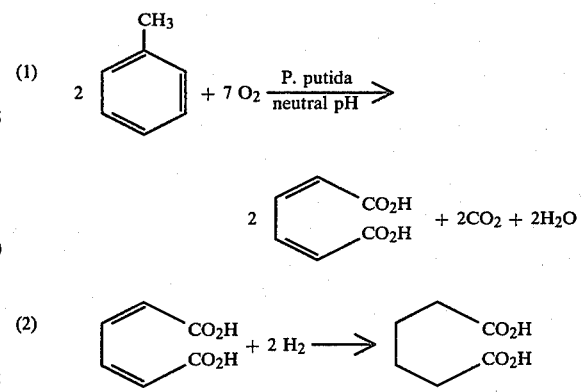

In the FIGURE, a stream of nutrients/water is fed through line 10 and air is fed through line 11 into cell preparation unit 15. As described more fully in the Examples, after the desired concentration of cell growth (e.g., P. putida) has been induced, the induced cells are passed as seed culture via line 12 to fermentor unit 20. Ammonia, oxygen and toluene are charged as separate streams to fermentor unit 20 by means of lines 21, 22 and 23, respectively. The pH in fermentor unit 20 is maintained at approximately neutral pH.

Fermentation broth is withdrawn continuously from fermentor unit 20 and passed via line 24 into cross-flow ultrafiltration module unit 25. Whole cell-containing retentate is recovered continuously from module unit 25 and recycled through line 26 to fermentor unit 20. Cell-free ammonium muconate-containing permeate is recovered continuously from module unit 25 and charged via line 27 to unit 30.

Sulfuric acid is entered into unit 30 through line 31 to precipitate muconic acid in the free acid form. The muconic acid is recovered by filtration, washed, dried, admixed with acetic acid, and passed through line 32 to hydrogenation unit 35.

The permeate in unit 30 is then treated with calcium carbonate solution by means of line 33 to precipitate calcium sulfate. The calcium sulfate precipitate is recovered via line 34 as a byproduct of the process. The resultant permeate fermentation broth in unit 30 is recycled via line 36 to fermentor unit 20.

Hydrogenation unit 35 is pressured with hydrogen via line 37, and muconic acid is converted to adipic acid in the presence of a hydrogenation catalyst such as Raney nickel. An adipic acid/acetic acid product mixture is transferred through line 38 to distillation unit 40. Acetic acid is separated as distillate via line 41, and adipic acid slurry is recovered through line 42 and subjected to water-washing and recrystallization or other purification means.

As noted in the Background Of The Invention section above, the microbiological oxidation of toluene to accumulated muconic acid requires the construction of mutant strains of microorganisms, e.g., as exemplified by *Pseudomonas putida* Biotype A strain ATCC 31,916.

This type of mutant strain can be provided by a process for microorganism construction which comprises (1) culturing microorganism species selectively to provide strain A1 which metabolizes toluene by the ortho pathway via cathechol to muconic acid, and which subsequently metabolizes the resultant muconic acid via β-ketoadipate to biomass and carbon dioxide; (2) continuously and selectively culturing strain A1 for rapid growth on toluene as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a non-selective carbon source and excess benzoate; (6) isolating cells from single small colonies, and culturing the cell isolates and selecting a strain A3, wherein strain A3 converts toluene to muconic acid and lacks active muconate lactonizing enzyme.

The starting microorganism can be any organism capable of growth on toluene and which possesses a cathechol 1,2-oxygenase, e.g., a Pseudomonad. A variety of naturally occurring organisms have these traits including some members of the species *Pseudomonas putida, Pseudomonas aeruginosa, Pseudomonas fluorescens;* some members of the genera Azotobacter and Nocardia; and a number of unclassified fungi (both molds and yeasts).

The preferred constructed microorganisms are those described in copending patent application Ser. No. 287,344 (incorporated by reference), which possess a novel combination of enzymes which include (1) dihydrodihydroxybenzoate dehydrogenase enzyme; and (2) catechol 1,2-oxygenase enzyme with activity that is not inhibited in the presence of less than about five gram/liter of muconic acid in a growth medium.

Illustrative of suitable microorganisms are constructed strains of fluorescent Pseudomonads each of which has the following characteristics:
  (a) possesses catechol 1,2-oxygenase enzyme with activity that is not inhibited in the presence of a low level of muconic acid in a growth medium;
  (b) lacks substantially catechol 2,3-oxygenase enzyme;
  (c) lacks functional muconate lactonizing enzyme;
  (d) cells are rod shaped, vigorously motile and polarly flagellated; and
  (e) cells grow well on p-hydroxybenzoate.

Employing one of the constructed microorganisms described above for the production of muconic acid from toluene, the rate of toluene conversion typically is about 0.8-1.2 grams of muconic acid produced per dry weight gram of cells per hour. The conversion of toluene proceeds readily at a dry weight cell concentration of 1-3 grams per liter, with a resultant muconic acid production rate of 0.4-2 grams per liter per hour.

Under optimal conditions, the muconic acid accumulation limit can approach up to about 50 grams of muconic acid per liter of growth medium. The microbiological oxidation step of the present invention process normally is conducted at ambient temperatures up to about 31° C. The muconic acid at a concentration between about 10-45 grams/liter in the cell-free ammonia-neutralized aqueous fermentation medium is precipitated with sulfuric acid or phosphoric acid. The precipitated muconic acid (solubility at pH of 1-2, about 0.07% at 20° C.) is filtered, washed and dried. In a further embodiment of the present invention as shown in the FIGURE, the muconic acid is admixed with a solvent medium such as acetic acid (e.g., to form a 40 weight percent muconic acid/acetic acid slurry solution), and then treated under hydrogenation conditions to yield adipic acid.

The acidic filtrate (pH of 1-2) is neutralized with a basic reagent (e.g., calcium carbonate) to yield a precipitated salt (e.g., calcium sulfate with a solubility of 0.2 weight percent at 20° C.). The salt is recovered as a byproduct of the overall process (via line 34 in the FIGURE).

The resultant fermentation broth is sterilized and recycled to the bioreactor. The bioconversion system can be operated in a continuous mode, without the continuous production of a waste byproduct stream.

The following examples are further illustrative of the present invention. The components and specific ingredients are presented as being typical, and various modifications can be derived in view of the foregoing disclosure within the scope of the invention.

For cultivation, carbon sources such as glucose, succinate, acetate or toluene are added aseptically prior to inoculation. Incubation conditions are in 250 ml shake flasks. Shaking is in a rotary shaker with temperature controlled at 28° C.

Growth is typically measured by determining the turbidity of the cell suspension in a Klett-Summerson Colorimeter using the #66 red filter. One Klett unit is equivalent to $3 \times 10^6$ cells per ml or 17.5 mg wet weight per liter or 3.52 mg dry weight per liter. Muconic acid salt is measured at 257 nm with a U.V. spectrophometer.

Cultures are stored under liquid nitrogen.

EXAMPLE I

This Example illustrates the construction of a strain of microorganism which oxidizes toluene via the ortho (β-ketoadipate) pathway.

A series of mutants which metabolize toluene through the ortho pathway is constructed by first blocking the meta pathway and then isolating phenotypic revertants which have reacquired the ability to grow on benzoate. Strains possessing a meta pathway block are isolated after penicillin plus D-cycloserine enrichment for organisms which fail to grow on benzoate. Some isolates are then spotted into agar plates and incubated in the presence of toluene. Virtually all isolates revert to growth on toluene. The plates are sprayed with 10 mM catechol and approximately 25% of the revertants are found not to produce 2-hydroxymuconic semialdehyde. None of the colorless revertants are found to possess an active catechol 2,3-oxygenase following induction with toluene.

It has been shown by Worsey and Williams, J. Bacteriol. 130, 1149 (1977) that growth on benzoate tends to cure a population of its TOL plasmid because the ortho pathway supports a higher growth rate. Since toluate can only be metabolized via the meta pathway, an alternative way to cure a population of its TOL plasmid is to use the penicillin plus D-cycloserine procedure to enrich for cells unable to grow on toluate.

Both these techniques are used in succession followed by counter-selection for growth on toluene. A strain designated MW 1200 is first cultured on toluene. A small portion (0.05 ml) of this culture is transferred to 50 ml of benzoate medium. After growth on benzoate the cells are transferred to toluate and incubated for approximately one hour. Penicillin and D-cycloserine are then added as described above and the incubation is continued for four to six hours. Cells are harvested, washed and transferred to a toluene containing medium.

After growth on toluene the cells are plated on benzoate agar and incubated for 48 hours, and a number of large colonies and a few small colonies are formed. After spraying with catechol it is found that all of the small colonies turn yellow (indicating the presence of the meta pathway) but none of the large colonies do. Large colonies are picked and cultured and it is found that following growth on toluene, these strains contain no functional 2,3-oxygenase but are fully induced for the 1,2-oxygenase. These strains metabolized toluene by the ortho pathway. One isolate, designated MW 1210, is employed in Example II.

EXAMPLE II

This Example illustrates the construction of a *Pseudomonas putida* Biotype A strain ATCC No. 31,916 type of mutant strain.

Strain MW 1210 of Example I is subjected to continuous cultivation with toluene as the sole source of carbon. Initially a dilution rate of 0.15 hours$^{-1}$ is employed. After the culture had stabilized, the dilution rate is increased successively to 0.25 hour$^{-1}$, 0.34 hour$^{-1}$, and 0.46 hour$^{-1}$. An isolate is made from the cells which dominates the culture at this latter dilution rate. This strain is then used to construct a strain which accumulates muconic acid to greater than one gram per liter.

The above strain is cultured overnight in liquid medium on toluene as the sole source of carbon, then benzoate is added to a level of 5 mM and the incubation is continued for approximately 1 hour. Penicillin G and D-cycloserine are added at concentrations of 12 and 0.1 mg/ml respectively. The antibiotic incubation is continued for approximately 5 hours. The cells are then harvested by centrifugation and washed twice with sterile de-ionized water. An aliquot of these cells is transferred to fresh medium containing 0.5 mM p-hydrobenzoate as a sole source of carbon, and the medium is incubated overnight. The procedure is repeated starting with induction with benzoate.

After 6 cycles those cells present in the culture after overnight growth on p-hydroxybenzoate are diluted and plated on an agar medium containing 0.5 mM succinate and 5.0 mM benzoate as sole sources of carbon. After 36 hours incubation the plate shows a mixture of large and small colonies. Cells from a number of small colonies are cultured in liquid medium, induced with toluene and tested for their ability to accumulate muconic acid. Isolate strains which accumulate muconic acid are identified.

EXAMPLE III

This Example illustrates the present invention process as a continuous fermentation system with cell recycle and fermentation broth recycle for the production of muconic acid from toluene.

A. Inoculum Preparation

A *Pseudomonas putida* Biotype A strain ATCC No. 31,916 type of mutant strain culture (regular "NO" medium aqueous culture in polypropylene vial stored in liquid nitrogen) is thawed and transferred (1–1.5 ml) to a 250 ml shake flask containing 50 ml of regular "NO" medium (Table I) with 5 mM sodium succinate as the growth carbon source, and is incubated at 30° C. (250 RPM) for nine hours to an optical density of 50–60 klett units.

The 50 ml culture is transferred to a 2.5 liter shake flask containing one liter of LP-1 medium (Table I) with 20 mM sodium acetate as the carbon source and three polypropylene vials each with one ml toluene as the inducer, and is incubated at 30° C. (250 RPM) for 15 hours to an optical density of 60–90 klett units. The one liter culture is then inoculated into a 16 liter steam sterilizable fermentor (New Brunswick Scientific, Model SF 116) containing 11.5 liters of LP-1 medium with 20 mM of sodium acetate to start fermentation.

B. Enzyme Induction

After the inoculation toluene is supplied to the fermentor medium in vapor phase via air-stripping at an air-toluene vapor rate of 125 cc/min. The fermentation temperature is controlled at 30° C., the pH at 6.9 with 10N ammonium hydroxide and 6N sulfuric acid solution, and a dissolved oxygen level at 30–100% saturation with 500 to 600 RPM agitation and 5 l/min aeration (approximately 0.5 VVM). Pluronic L61 polyol (BASF) is used as an antifoam agent.

As the optical density of the fermentation medium reaches 60–90 klett units (about 6–9 hours after inoculation), an aqueous solution containing 10 wt % acetic acid, 0.245 wt % $KH_2PO_4$ and 0.128 wt % $Na_2HPO_4$ is added to the fermentor medium at a rate of 0.4 ml/min. The air-toluene vapor rate is increased to 250 cc/min and then increased to 500 cc/min as the optical density reaches 250 klett units. The fed batch mode of fermentation is continued for 21 hours and the muconic acid product concentration reaches 12.6 g/l at a cell concentration of 2.1 g/l. The fermentation is then converted to a continuous operation with a cell recycle mode of operation.

C. Continuous/Cell Recycle

Starting the continuous/cell recycle operation, fresh membrane-sterilized LP-1 medium with 1.04 g/l acetic acid, 0.0256 g/l $KH_2PO_4$ and 0.0134 g/l $Na_2HPO_4$ concentration is pumped (FMI piston pump) into the fermentor at a rate of 38.3 ml/min. The fermentation broth is pumped from the fermentor with an internal circulation pump (Micro gear pump) to a Romicon® hollow tube ultrafilter with a polysulfone type ultrafiltration membrane (PM-100; molecular weight cutoff of 100,000). Total membrane area is 1.1 ft$^2$ (50 tubes in a 1.0"×25" cylindrical polypropylene cartridge).

The fermentation broth with cells is "cross-flow" filtered by the ultrafilter controlled at a permeate (clean, cell-free product stream) rate of 36 to 39 ml/min. The fermentation broth with cells is continuously circulated "through" the ultrafilter at an internal circulation rate of 4.5 l/min and a pressure drop of five to ten psig across the ultrafiltration membrane. Three hours after starting the continuous/cell recycle operation without purge, the cell concentration reaches 2.8 g/l. A purge stream at a rate of 2.7 ml/min is then maintained during the continuous/cell recycle run. After initial decrease, the product concentration in the cell-free permeate stream is maintained at 6.8 to 7.0 g/l at a permeate rate of 38 ml/min. The air-toluene vapor rate is increased to 1000 ml/min.

During this type of steady state continuous/cell recycle mode of operation, a reactor productivity of 1.4 g muconic acid/l/hr (0.20 hr$^{-1}$×6.9 g/l) is achieved and a specific productivity of 0.58 g muconic acid/g cells/hr (6.9 g/l×0.2 hr$^{-1}$/2.4 g/l) is maintained.

D. Product Recovery And Fermentation Broth Recycle

The continuous operation is modified to include a product recovery procedure and a recycle of fermentation broth.

In the manner previously described, a solution of concentrated $H_3PO_4$ is added to the cell-free permeate to precipitate the muconic acid product. The precipitate is separated by filtration.

The acidic filtrate is neutralized with $BaCO_3$ which results in the formation and precipitation of $BaHPO_4$ solids. The solids are separated by filtration.

The resultant fermentation broth filtrate, which contains $(NH_4)_2CO_3$ solute, is emulsified with toluene and air, sterilized, and then recycled to the fermentor. The quantity of $NH_4OH$ fed to the fermentor is reduced by an amount corresponding to the molar input of $(NH_4)_2CO_3$ contained in the recycled fermentation broth.

E. Adipic Acid Production

Muconic acid is dissolved in acetic acid to form a 40% muconic acid/acetic acid slurry solution.

The slurry solution is fed to a hydrogenation fixed-bed reactor (at 102° C. and 3 atm) with Pd/C as the catalyst.

The hydrogenation product solution is flashed and distilled to separate acetic acid. The heavy end slurry, which consists substantially of adipic acid, is washed to remove trace acetic acid, and dried.

TABLE I
MEDIUM COMPOSITIONS
A. Regular "NO" Medium

| Chemicals | (g/l) | (mM) |
|---|---|---|
| $Na_2HPO_4$ | 7.1 | 50 |
| $KH_2PO_4$ | 13.6 | 100 |
| $(NH_4)_2SO_4$ | 2.25 | 17 |
| $MgSO_4.7H_2O$ | 0.246 | 1 |
| $CaCl_2$ | 0.0111 | 0.1 |
| $FeSO_4.7H_2O$ | 0.00278 | 0.01 |

With appropriate growth carbon source in deionized water.

B. Modified "NO" Medium

| Chemicals | (g/l) | (mM) |
|---|---|---|
| $Na_2HPO_4$ | 7.1 | 50 |
| $KH_2PO_4$ | 13.6 | 100 |
| $(NH_4)_2SO_4$ | 0.281 | 2.1 |
| $MgSO_4.7H_2O$ | 0.738 | 3 |
| $CaCl_2$ | 0.0222 | 0.2 |
| $FeSO_4.7H_2O$ | 0.00834 | 0.03 |

With appropriate growth carbon source in deionized water.

C. LP-1 Medium

| Chemicals | (g/l) | (mM) |
|---|---|---|
| $Na_2HPO_4$ | 1.42 | 10.0 |
| $KH_2PO_4$ | 2.72 | 20.0 |
| $(NH_4)_2SO_4$ | 0.749 | 5.67 |
| $MgSO_4.7H_2O$ | 0.738 | 3.0 |
| $CaCl_2$ | 0.0222 | 0.2 |
| $FeSO_4.7H_2O$ | 0.00834 | 0.03 |

With appropriate growth carbon source in deionized water.

EXAMPLE IV

This Example further illustrates an invention continuous fermentation system for production of muconic acid from toluene.

The inoculum preparations, enzyme induction and continuous/cell recycle operational procedures are the same as in Example III except for the following changes:

(1) The total ultrafiltration membrane area is increased to 2.2 ft$^2$ (two Romicon ® hollow tube ultrafilters in parallel, PM-100 membrane). The ultrafilter membrane is sanitized with 5% phosphoric acid and 90% ethanol followed by sterilized deionized water washing.

(2) The acetic acid concentration in the fresh feed medium during continuous/cell recycle operation is reduced to 0.696 g/l, and the $(NH_4)_2SO_4$ concentration to 0.0922 g/l in modified "NO" medium.

(3) The non-growth carbon toluene in liquid form is pumped directly into the fermentor via an FMI rotary piston micro pump at a rate of 0.278 ml/min during the continuous/cell recycle operation.

The "fed-batch" mode of fermentation is performed for 24 hours before changing to continuous/cell recycle operation. The fermentation is controlled at 30° C., a pH at 6.9 with 10N sodium hydroxide solution, and dissolved oxygen at 30–100% saturation with 550–600 RPM agitation and 5 l/min aeration. The fermentor working volume is controlled at 11.5 liter with an NBS level controller. The cell free permeate rate from the ultrafilter is controlled at 55–57 ml/min and a cell purge rate from the fermentor at 2.5 ml/min throughout the continuous/cell recycle operation. This is equivalent to a dilution rate of 0.3 hr$^{-1}$.

The run is terminated after six days of stable operation of the continuous flow, stirred-tank ultrafiltration reactor (with cell recycle). Steady state production (over six days) of muconic acid from toluene at a reactor productivity of 0.8 to 1.0 g/l/hr. (STY) and a specific productivity of 0.25–0.35 g muconic acid/g dry cell/hr is achieved.

What is claimed is:

1. In a microbial bioconversion process in which a non-growth aromatic hydrocarbon substrate in an aqueous fermentation zone is bio-oxidized by intracellular enzyme activity of whole cells to an extracellular water-soluble carboxylic acid product having a molecular weight less than about 1000, and recovering said carboxylic acid product the improvement which comprises (1) continuously feeding an aqueous nutrient-limited stream into the fermentation zone; (2) continuously withdrawing whole cell-containing fermentation broth from the fermentation zone; (3) continuously passing the withdrawn fermentation broth through a cross-flow membrane filtration zone; (4) recovering a whole cell-containing retentate stream from the filtration zone, and recycling the retentate stream to the fermentation zone; and (5) recovering a cell-free product-containing permeate stream from the filtration zone, separating the product from the permeate stream, and recycling the resultant permeate stream to the fermentation zone.

2. A process in accordance with claim 1 wherein the aromatic hydrocarbon substrate is toluene.

3. A process in accordance with claim 1 wherein the carboxylic acid product is muconic acid.

4. A process in accordance with claim 1 wherein the nutrient stream is nitrogen-limited.

5. A process in accordance with claim 1 wherein the nutrient stream is phosphorus-limited.

6. In a microbial bioconversion process in which a toluene substrate in an aqueous fermentation zone is bio-oxidized by intracellular enzyme activity of Pseudomonad whole cells to an extracellular muconic acid product in a fermention zone during a bioconversion period and recovering said muconic acid product, the improvement which comprises (1) neutralizing the acidic pH conditions in the fermentation zone by the addition of ammonia during the bioconversion period; (2) continuously feeding an aqueous nutrient-limited stream into the fermentation zone; (3) continuously withdrawing whole cell-containing fermentation broth from the fermentation zone; (4) continuously passing the withdrawn fermentation broth through a cross-flow membrane filtration zone; (5) continuously recovering a whole cell-containing retentate stream from the filtration zone, and recycling the retentate stream to the fermentation zone; (6) continuously recovering a cell-free ammonium muconate-containing permeate stream from the filtration zone; (7) adding sulfuric acid or phosphoric acid to the permeate stream to precipitate muconic acid; (8) separating the muconic acid precipitate product from the permeate stream, and subsequently treating the permeate stream with a basic reagent selected from the group consisting of metal hydroxides, oxides and carbonate compounds which causes the precipitation of a water-insoluble metal salt; and (9) separating the metal salt precipitate to form a resultant permeate stream containing a water-soluble ammonium compound, and recycling the said permeate stream to the fermentation zone.

7. A process in accordance with claim 6 wherein the aqueous nutrient stream in step(2) is phosphorus-limited to stabilize cell growth.

8. A process in accordance with claim 6 wherein the filtration zone comprises an ultrafiltration hollow fiber module.

9. A process in accordance with claim 6 wherein the filtration zone comprises an ultrafiltration plate and frame module.

10. A process in accordance with claim 6 wherein the basic reagent in step(8) is a calcium compound.

11. A process in accordance with claim 6 wherein the basic reagent in step(8) is calcium carbonate.

12. A process in accordance with claim 6 wherein the bioconversion is accomplished by *Pseudomonas putida* Biotype A strain ATCC 31,916.

13. A process in accordance with claim 6 wherein the bioconversion is accomplished by a fluorescent Pseudomonas microorganism having the following characteristics:
(a) possesses catechol 1,2-oxygenase enzyme with activity that is not inhibited in the presence of a low level of muconic acid in a growth medium;
(b) lacks substantially catechol 2,3-oxygenase enzyme;
(c) lacks functional muconate lactonizing enzyme;
(d) cells are rod shaped, vigorously motile and polarly flagellated; and
(e) cells grow well on p-hydroxybenzoate.

* * * * *